(12) United States Patent
Jensen

(10) Patent No.: US 6,309,221 B1
(45) Date of Patent: Oct. 30, 2001

(54) COMPOSITIONS, METHODS AND KITS FOR HEMOSTASIS AND SEALING OF PULP DURING INVASIVE DENTAL PROCEDURES

(75) Inventor: Steven D. Jensen, Riverton, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 09/687,117

(22) Filed: Oct. 13, 2000

(51) Int. Cl.$^7$ ....................................................... A61C 5/04
(52) U.S. Cl. .................................. 433/226; 433/217.1
(58) Field of Search ................................. 433/217.1, 226, 433/228

(56) References Cited

U.S. PATENT DOCUMENTS

| | | | |
|---|---|---|---|
| 2,454,746 | 11/1948 | Ullyot | 260/563 |
| 4,321,038 | 3/1982 | Porteous | 433/136 |
| 4,465,462 | 8/1984 | Ticknor | 433/136 |
| 4,617,950 | 10/1986 | Porteous et al. | 132/91 |
| 4,871,311 | 10/1989 | Hagne | 433/136 |
| 4,892,482 | 1/1990 | Lococo | 433/136 |
| 4,911,927 | 3/1990 | Hill et al. | 424/443 |
| 5,104,317 | 4/1992 | Riazi | 433/136 |
| 5,540,588 | 7/1996 | Earle | 433/136 |
| 5,635,162 | 6/1997 | Fischer | 424/49 |
| 5,750,141 | 5/1998 | Roberts et al. | 424/449 |
| 5,899,694 | 5/1999 | Summer | 433/136 |
| 6,071,528 | * 6/2000 | Jensen | 424/407 |

OTHER PUBLICATIONS

K. R. Payne, Ph.D., Synthesis of Adrenaline and Related Compounds, The Industrial Chemist, Nov., 1961, pp. 523–527.

Forsyth et al., Blood Pressure Responses to Epinephrine–Treated Gingival Retraction Strings in the Rhesus Monkey, JADA, vol. 78, Jun. 1969, pp. 1315–1319.

*The Merck Index,* pp. 613 and 1350, Twelfth Edition, 1996.

* cited by examiner

*Primary Examiner*—Cary E. O'Connor
(74) *Attorney, Agent, or Firm*—Workman, Nydegger & Seeley

(57) ABSTRACT

Compositions, methods and kits for providing hemostasis and sealing of exposed tooth pulp and/or pink dentin. The inventive methods and kits employ propylhexedrine as a hemostatic agent, such as in the form of an aqueous composition of propylhexedrine hydrochloride, and an adhesive sealant composition. The propylhexedrine solution is advantageously applied to the exposed pulp and pink dentin by means of a cotton pellet or other absorbent applicator. The adhesive sealant composition is advantageously applied to exposed pulp and pink dentin, which has been previously treated with the propylhexedrine solution, by means of a syringe. The adhesive sealant composition may include an alkyl methacrylate having an oxyphosphorus group, a polymerization initiator and an antimicrobial agent, such as calcium hydroxide. The adhesive sealant composition can be polymerized in situ and is used to prevent ingress by microorgaism into an area of the tooth being treated.

24 Claims, No Drawings

COMPOSITIONS, METHODS AND KITS FOR HEMOSTASIS AND SEALING OF PULP DURING INVASIVE DENTAL PROCEDURES

BACKGROUND OF THE INVENTION

1. The Field of the Invention

The present invention is in the field of restorative dentistry. More particularly, the invention is in the field of compositions, methods and kits for hemostasis and sealing of dental pulp and/or dentin during the excavation of deep cavities, preparation for the placement of crowns, and other invasive dental procedures that expose the pulp and/or pink dentin. The compositions, methods and kits employ propylhexedrine as a hemostatic agent together with an adhesive composition to seal and at least partially fill a hollow within a tooth.

2. The Relevant Technology

During invasive dental procedures, such as the excavation of deep cavities or placement of crowns, it is customary to use a cap or liner over the exposed pulp or dentin preparatory to receiving the final filling material. Dental liners may be applied before the application of a filling material to, e.g., act as a barrier against ingress of bacteria, which can cause decay, to stimulate reparative dentin, and/or to provide thermal insulation. Pulp caps are more particularly used when both pink dentin and the pulp are exposed.

Dental liners can be used with virtually any type of filling material, although they are more typically used where the filling material comprises metal amalgam. Since composite fillings typically form a relatively good seal with the dentin and enamel, it is generally not necessary to use dental liners with composite fillings unless the preparation extends into, or is near, a pulpal exposure. Dental liners are, however, generally needed with metal amalgam fillings since metal amalgam fillings typically do not seal the exposed interior of the tooth from accessibility by bacteria. Such liners may also be used to stimulate reparative dentin provide thermal insulation.

The same dental material utilized for liners is also conventionally utilized for pulp capping to protect the pulp after excavating deep caries which result in penetration near or into the pulp chamber. The pulp and the adjacent tissue, the pink dentin, are the living portion of a tooth and accordingly are highly prone to destruction by pathogenic contamination. The failure to properly seal the pulp chamber and pink dentin can lead to bacterial infection of the pulp. Such infections are very difficult for the body to fight and may often lead to serious infections of the teeth and surrounding bone.

Since the pulp and pink dentin are surrounded by hard enamel or filling material, infected dental tissues are incapable of expanding with the inflammation caused by the infection. Thus, tooth infections may lead to circulatory "back pressure" which, in turn, can often restrict blood flow to the infected area. Restriction of the blood supply to the tooth greatly inhibits the ability of the pulp to fight off the infection since needed macrophages and antibodies are inhibited or prevented from entering into the infected area. Infections of the pulp generally cause the tooth to die. Thus, it was generally thought that "exposed pulp is a dumed organ". Accordingly, it is generally crucial when exposing the pulp during an invasive dental procedure to protect the pulp from infection by utilizing a pulp cap as a barrier against the ingress of bacteria and/or to initiate reparative bridge formation for a biological seal.

In addition to sealing the pulp cavity to prevent the ingress of bacteria, it may also be advantageous to stimulate reparative bridge formation. To increase the likelihood of reparative bridge formation, compositions which contain calcium, such as calcium hydroxide, are conventionally utilized since the calcium is believed to be incorporated as hard tooth material by the living pink dentin. Calcium hydroxide compositions may also provide antibacterial activity since the high pH of the calcium hydroxide kills bacteria.

Exposure of the pulp often occurs as a result of excavating deep caries in preparation for placing a filling or crown. Restorative dental procedures related to fillings and crowns may require the use of harsh chemicals which can result in postoperative sensitivity if the chemicals contact the pulp. The steps for restorative dental procedures related to fillings and crowns if a deep preparation or exposure has been excavated, generally involve disinfecting the area with a disinfectant, drying the area, placing a pulp cap at or near the opening into the pulp chamber, etching the area, priming the area and then applying a bonding resin for a composite or crown or placing a metal amalgam filling. Thus, a properly applied pulp cap not only minimizes the likelihood and degree of postoperative sensitivity from chemicals or bacteria in the dentin tubules near or in the pulp, but the postoperative inflammatory response is also reduced, thus promoting healing and predictable nonendodontic success.

Although the survivability of a tooth having an exposed or nearly exposed pulp can be increased by the use of a pulp cap, conventional pulp caps generally fail to adequately seal a treated area and generally have a deleterious impact on the retention of restorations. Moreover, conventional liners may have a negative impact on a bonded restoration due to the generally low strength of the liner, which is significantly less than that of the covering restorative material. Conventional liners can easily become dislodged during placement of the filling material, during shaping of the filling material, or as a result of subsequent jarring or harsh manipulation of the tooth.

In addition to the poor adhesion of some dentin liners and pulp caps, particularly those which include calcium hydroxide, adhesion may further be inhibited due to bleeding and oozing of fluid from the pulp and/or dentinal tubules. Although there are a number of astringents on the market, such as those based on salts of aluminum, iron and zinc, such astringents are not used because they can cause tremendous pain and will generally kill the pulp, thus requiring a root canal. Bleeding and oozing of fluid from the pulp and/or dentinal tubules can also contaminate the dentin liner or pulp cap.

Accordingly, it would be an improvement in the art of restorative dentistry to provide compositions, methods and kits that enabled more reliable sealing and adhesion to the dentinal tissue so as to provide a reliable barrier to the ingress of bacteria into the pulp and/or pink dentin and thereby prevent infection of the tooth.

More specifically, it would be an important improvement in the art of restorative dentistry to provide compositions, methods and kits which could arrest the bleeding of the pulp and/or pink dentin subsequent to exposure of the pulp and/or pink dentin and preparatory to the application of an adhesive sealant or filling material to the dentin.

It would be a further improvement in the art to provide compositions, methods and kits which included a hemostatic agent that was capable of arresting the bleeding of exposed pulp and/or pink dentin which did not result in the death of the pulp.

Finally, it would yet be an improvement in the art to provide compositions, methods and kits which included an adhesive liner, capping and/or filling material capable of forming a strong and reliable seal against the dentin in order to form a reliable barrier against the ingress of microorganisms into the pulp and/or pink dentin.

Such compositions, methods and kits for providing hemostasis of the pulp and/or pink dentine and a strong and reliable seal against the dentin are disclosed and claimed herein.

SUMMARY AND OBJECTS OF THE INVENTION

The present invention relates to compositions, methods and kits for hemostasis and sealing of dental pulp and/or dentin during invasive dental procedures that expose the pulp and/or pink dentin. Such invasive procedures typically include, but are not limited to, the excavation of cavities and the preparation of teeth for the placement of crowns. The compositions utilized within the inventive methods of the present invention may advantageously be sold or packaged together as a kit. The inventive kit preferably includes a hemostatic composition and an adhesive liner, cap, or filling material.

The hemostatic composition preferably includes propylhexedrine. Propylhexedrine is a vasoconstrictor having strong vasoconstriction properties similar to epinephrine but without the harsh side effects of epinephrine. Epinephrine, which is typically used in the form of epinephrine hydrochloride, is commonly used as a vasoconstrictor in a wide variety of applications but has a tendency to cause systemic, rather than merely localized, physiological responses. For example, epinephrine is known to produce the side effect of increasing a person's pulse rate and blood pressure. This is not surprising since epinephrine is the principal sympathomimetic hormone produced by the adrenal medulla. Hence, epinephrine is often referred to as "adrenaline", the "fight or flight" hormone, which is associated with fear, excitement, anxiety, or other similar emotional and biochemical responses which result in increased pulse rate, elevated blood pressure, and accelerated metabolism. It is therefore not commonly used as a hemostatic agent in treating exposed pulp and pink dentin.

Propylhexedrine, on the other hand, has been shown to have a much more localized vasoconstricting effect than epinephrine. Moreover, propylhexedrine is not an adrenal hormone like epinephrine and, hence, does not have the same hormonal effects on a person's biochemistry, pulse, and heart rate.

In order to make propylhexedrine more compatible with the aqueous environment of exposed dental pulp and pink dentin, propylhexedrine is advantageously utilized in the form of a salt, such as propylhexedrine hydrochloride. Propylhexedrine hydrochloride is water-soluble and may be readily dissolved in water or other highly polar solvents such as DMSO, glycerin, or alcohol. Propylhexedrine, when not in its salt form, is readily soluble in alcohol, chloroform, and ether.

In a preferred embodiment, the propylhexedrine is applied to the pulp and/or pink dentin in an aqueous solution, such as an 80% solution of propylhexedrine hydrochloride in water. Whereas the propylhexedrine hydrochloride solution may be applied to the pulp or dentin in any desired manner, a preferred method of application is by means of a small cotton swab or pellet sized so as to be at least partially insertable into the hollow or cavity of the tooth being treated. Upon exposure of the pulp and/or dentin, such as by means of dental burr or drill, a cotton pellet that includes a sufficient quantity of aqueous propylhexedrine hydrochloride solution is advantageously placed into the hole or cavity of the tooth for a period of time sufficient to cause hemostasis and stoppage of the bleeding or oozing from the pulp and/or dentinal tubules. After a desired level of hemostasis has been effected, the cotton pellet is removed and any remaining blood or fluid may advantageously removed by aspiration of the tooth and surrounding area.

Thereafter, an appropriate adhesive sealing material is preferably applied to the dentin so as to seal the dentin and/or pulp and provide a barrier to the ingress of microorganisms. Thus, the second component in the inventive kits of the present invention includes an adhesive sealant composition. The adhesive sealant composition may comprise any conventional dentin liner, pulp cap, or dental filling material. In a preferred embodiment, the adhesive sealant composition includes a liner, cap, or filling material based on the compositions disclosed in U.S. Pat. No. 6,071,528 to Jensen. For purposes of disclosing preferred adhesive sealant compositions within the scope of the invention, the foregoing patent is incorporated herein by specific reference. A preferred adhesive sealant composition manufactured according to U.S. Pat. No. 6,071,528 is available from Ultradent Products, Inc. in South Jordan, Utah, under the trade name ULTRA-BLEND. Other products of Ultradent Products, Inc. that are known to adhesively seal dentin include ULTRASEAL XT and PERMAFLO.

The adhesive sealant composition is preferably antimicrobial and more preferably provides for reparative bridge formation of the live dentin. The preferred adhesive sealant composition comprises at least an alkyl methacrylate having an oxyphosphorus group, a polymerization initiator, and an antimicrobial agent, preferably a component such as calcium hydroxide that provides for reparative dentin stimulation. The adhesive sealant composition may also comprise other additives, such as fillers and diluent monomers.

Of course it is certainly within the scope of the invention to utilize any sealant, liner, pulp cap, or filling material known in the art in combination with propylhexedrine during tooth restoration procedures. At a minimum, it will be advantageous for the adhesive sealants to provide a strong and reliable seal which prevents the ingress of microorganisms into the pulp and/or pink dentin. Examples of adhesive sealants or polymerizable filler materials known in the art that may be used in the kits of the prevent invention are set forth in U.S. Pat. No. 3,997,504 to Plymale, U.S. Pat. No. 5,055,497 to Okada et al., U.S. Pat. No. 4,657,941 to Blackwell et al., U.S. Pat. No. 4,813,876 to Wang, U.S. Pat. No. 4,872,936 to Engelbrecht, U.S. Pat. No. 5,547,379 to Hasel, U.S. Pat. No. 5,944,527 to Hasel, U.S. Pat. No. 4,544,359 to Wakrine, and U.S. Pat. No. 5,425,641 to Fischer. For purposes of disclosing adhesive sealant compositions, the foregoing patents are incorporated herein by specific reference.

It is also within the scope of the invention to provide an antimicrobial composition that is applied to the pulp and/or pink dentin before application of the adhesive sealant. Even though it would certainly be within the scope of the invention to provide an antimicrobial agent in combination with propylhexedrine, it would be more preferable to apply the antimicrobial composition or agent to the exposed pulp and/or dentin subsequent to stopping or at least slowing the bleeding or oozing of fluid by means of the propylhexedrine-containing hemostatic composition.

Accordingly, it is an object of the present invention to provide compositions, methods, and kits that enable more reliable sealing and adhesion to the dentinal tissue so as to provide a reliable barrier to the ingress of bacterial into the pulp and/or pink dentin and thereby prevent infection of the tooth.

More specifically, it is an object of the invention to provide compositions, methods, and kits which can arrest the bleeding of the pulp and/or pink dentin subsequent to exposure of the pulp and/or pink dentin and preparatory to the application of an adhesive sealant or filling material to the dentin.

It is a further object and feature of the invention to provide compositions, methods, and kits which include a hemostatic agent that is capable of arresting the bleeding of exposed pulp and/or pink dentin which does not result in the death of the pulp.

It is yet an object of the invention to provide compositions, methods, and kits which include an adhesive liner, capping, and/or filling material capable of forming a strong and reliable seal against the dentin in order to form a reliable barrier against ingress of microorganisms in the pulp and/or pink dentin.

These and other objects, features and advantages of the present invention will become more fully apparent from the following description and appended claims, or may be learned by the practice of the invention as set forth hereinafter.

DETAILED DESCRIPTION OF THE PREFERRED EMBODIMENTS

I. INTRODUCTION

The present invention encompasses compositions, methods and kits for providing hemostasis and sealing of dental pulp and/or dentin during invasive dental procedures that expose the pulp and/or pink dentin. Invasive procedures that result in the exposure of pulp and/or pink dentin include, but are not limited to, the excavation of cavities and the preparation for the placement of crowns. The inventive kits include, and the methods utilize, propylhexedrine as a hemostatic agent in order to provide hemostasis of bleeding pulp and/or pink dentin prior to the application of an adhesive sealant composition. The inventive kits also include, and the methods utilize, an adhesive sealant composition in order to seal the pulp and/or pink dentin so as to prevent the ingress of microorganisms. Infection of the pulp can lead to painful abscesses and ultimately death of the pulp.

The adhesive sealant composition may comprise any composition capable of adhering to dentin, including but not limited to, adhesive liners, caps, and filling materials. The adhesive sealant compositions will preferably include an antimicrobial agent in order to kill any microorganisms that may have invaded the pulp and/or dentin prior to application of the sealant material. In the alternative, an antimicrobial composition may be applied prior to the application of the adhesive sealant material.

By first providing hemostasis of bleeding or oozing pulp and/or pink dentin, the compositions, kits and methods of the present invention are more effective in sealing the treated substrate from ingress by bacteria than when using adhesive sealants without a hemostatic agent. As will be discussed below, the most preferred adhesive sealant compositions are based on compositions disclosed in U.S. Pat. No. 6,071,528 to Jensen.

II. KITS FOR PROVIDING HEMOSTASIS AND SEALING OF DENTAL TISSUES

A. Hemostatic Compositions

The hemostatic compositions according to the present invention will, at a minimum, include propylhexedrine, either alone or in combination with a carrier solvent. The term "propylhexedrine", as used in the specification and the appended claims, shall refer to propylhexedrine and any salts or other derivatives of propylhexedrine, including but not limited to propylhexedrine hydrochloride.

Propylhexedrine is the preferred hemostatic agent because it is able to provide localized hemostasis of hemorrhaging blood vessels without causing the negative size effects of astringents, which typically cause extreme pain and even death of the pulp if applied directly to the pulp. Propylhexedrine is a vasoconstrictor and is superior to epinephrine, another known vasoconstrictor, which causes elevated heart rate and quickened pulse.

The chemical name for propylhexedrine is N,α-dimethylcyclohexaneethylamine (IUPAC name). It is known as β-cyclohexylisopropylmethylamine in U.S. Pat. No. 2,454,746 to Ullyot, which describes an earlier-used synthetic route for preparing propylhexedrine. Propylhexedrine is represented by the following chemical structure:

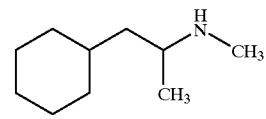

Propylhexedrine is a clear, colorless liquid having a characteristic amine-like odor. It volatilizes slowly at room temperature and solutions are alkaline when subjected to a litmus test. Propylhexedrine therefore absorbs carbon dioxide from the air in an acid-base reaction. The specific gravity is between 0.848 to 0.852. It boils at about 205° C. Propylhexedrine is only slightly soluble in water, with only 1 gram being dissolvable in 500 ml of water. On the other hand, 1 gram of propylhexedrine is soluble in 0.4 ml alcohol, 0.2 ml of chloroform, or 0.1 ml of ether. The hydrochloride form of propylhexedrine, formed by reacting one molar equivalent of propylhexedrine with one molar equivalent of hydrochloric acid, is soluble in water and is a crystalline solid at room temperature.

In order to provide propylhexedrine in a form that is readily compatible with blood and the aqueous and/or highly polar mineralized environment found in tooth pulp and dentin, the propylhexedrine will preferably be in the form of a salt, such as propylhexedrine hydrochloride. In a preferred embodiment, the propylhexedrine hydrochloride, or other form, salt or derivative thereof, will be dissolved within an appropriate carrier solvent. In the case of propylhexedrine hydrochloride, the carrier solvent will comprise water, either alone or in combination with other compatible solvents, such as alcohols or polyols.

The hemostatic compositions according to the present invention may include from about 0.1% to 100% by weight of propylhexedrine, preferably from about 10% to about 99% by weight propylhexedrine, more preferably from about 50% to about 95% by weight propylhexedrine, and most preferably from about 70% to about 90% by weight propylhexedrine.

B. Adhesive Sealant Compositions

The kits according to the present invention, in addition to including a hemostatic composition as described herein, shall also include an adhesive sealant composition, such as a liner, a cap or a restorative filling material. The adhesive sealant compositions within the scope of the invention will typically include one or more polymerizable adhesive monomers, one or more polymerization initiators, such a photoinitiator, and may optionally include one or more additional components, such as diluent monomers, antimicrobial agents, fillers or chemical initiators. The most preferred adhesive sealant compositions according to the invention include compositions disclosed in U.S. Pat. No. 6,071,528 to Jensen.

Other adhesive sealant compositions that may be included in the inventive kits are disclosed in U.S. Pat. No. 3,997,504 to Plymale, U.S. Pat. No. 5,055,497 to Okada et al., U.S. Pat. No. 4,657,941 to Blackwell et al., U.S. Pat. No. 4,813,876 to Wang, U.S. Pat. No. 4,872,936 to Engelbrecht, U.S. Pat. No. 5,547,379 to Hasel, U.S. Pat. No. 5,944,527 to Hasel, U.S. Pat. No. 4,544,359 to Waknine, and U.S. Pat. No. 5,425,641 to Fischer. As stated previously, the foregoing patents are incorporated herein by reference.

1. Adhesive Monomers

Even though it is within the scope of the invention to use any adhesive monomer known in the art, in a preferred embodiment, polymerizable adhesion monomers may be employed which comprise at least one alkyl methacrylate having at least one oxyphosphorus group. Oxyphosphorus alkyl methacrylates provide superior adhesion strengths, which reliably form an effective and liquid-tight seal, compared to other monomers. It has been found, for example, that the use of oxyphosphorus alkyl methacrylates yields adhesive sealant compositions that can form a seal without risk of failure due to being bumped by a dental tool or by being dislodged during instrumented shaping or contouring. When used in the form of a cap or liner, such compositions provide an effective back-up seal against the ingress from microorganisms beyond the protection provide by the filling material itself. Of course, it is certainly within the scope of the invention to utilize oxyphosphorus alkyl methacrylates within any adhesive sealant, including dental filling materials.

Preferred adhesion monomers are those which are stable in the presence of light-activated polymerization initiators, optional antimicrobial agents, and other additives such as fillers. Accordingly, preferred compositions are characterized as being capable of being polymerized in situ by initiation of a polymerization photoinitiator after the composition has been placed in contact with the substrate.

Utilizing adhesion monomers that are stable in the presence of a polymerization photoinitiator allows the adhesive sealant compositions to be utilized as a single component system or a one package composition and to be stable until polymerization is intentionally initiated. More specifically, the composition may be formed from constituents that, once mixed, thereafter yield a stable composition that is ready for storage and subsequent application directly to a substrate for in situ polymerization without the need for subsequent mixing. The primary advantage of such a system is increased efficiency for the dental practitioner. After a stable composition has been mixed, it will preferably maintain its capability of polymerizing and being useful as an adhesive sealant for at least about six months, more preferably at least about a year and most preferably at least about two years.

The most preferred oxyphosphorus alkyl methacrylate is bis glycerol methacrylate phosphate. Examples of other preferred oxyphosphorus alkyl methacrylates include, but are not limited to, bis 2-hydroxyethyl methacrylate phosphate, phosphate ester of p-hydroxyphenyl methacrylamide, phosphate ester of 3-hydroxypropylmethacrylate, and phosphate ester of 4-hydroxybutyl methacrylate. The oxyphosphorus alkyl methacrylate can be any alkyl methacrylate having an oxyphosphorus group or phosphorus acid group selected from the group consisting of:

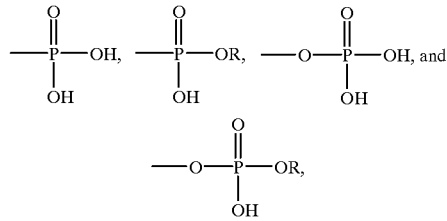

wherein R is preferably an alkyl, but which may also be an aryl.

In the case where the adhesive sealant includes an antimicrobial agent, the phosphorus alkyl methacrylate will preferably be essentially nonreactive with the antimicrobial agent. Mixtures and derivatives of any of the foregoing oxyphosphorus alkyl methacrylates are also within the scope of the invention. In addition to the above oxyphosphorus alkyl methacrylates, other oxyphosphorus alkyl methacrylates, or even alkyaryl methacrylates, are within the contemplation of the present invention and can be found by routine experimentation by reading the disclosure and practicing the invention.

In the case where the adhesive sealant composition includes one or more oxyphosphorus alkyl methacrylates, the adhesive sealant composition will preferably include oxyphosphorus alkyl methacrylate in a concentration of about 0.01% to about 90% by weight of the adhesive sealant composition, more preferably in a concentration of about 0.5% to about 30%, and most preferably in a concentration of about 1% to about 12% by weight of the adhesive sealant composition.

2. Antimicrobial Agents

The adhesive sealant compositions within the inventive kits may advantageously include one or more antimicrobial agents in order to eliminate microorganisms on contact when the adhesive sealant compositions are placed on the dental substrate. One advantage of killing microorganisms, such as bacteria, is that the pulp can more readily heal and form a reparative bridge.

Examples of antibacterial agents that can be utilized to prevent ingress by microorganisms and to kill microorganisms on the area being treated by the adhesive sealant composition include, but are not limited to, organohalogens, antibiotics, alkali metal hydroxides, alkaline earth metal oxides and alkaline earth metal hydroxides. Examples of antibacterial organohalogens include: 1,1'-hexamethylenebis(5(p-chlorophenyl)biguanide), cetyl pyridinium chloride, benzalkonium chloride and cetyl pyridinium bromide. Examples of suitable antibiotics include: 4'-sulfamoylsulfanilanilide, 3-amino-6-(2-(5-nitro-2-furyl)vinyl)pyridazine, trans-pseudomonic acid, xanithomycin, alpha-amino-p-toluene sulfonamide, alpha-azido benzyl penicillin, penicillin O, penicillin N, monopropionyl erythromycin and erythromycin 9(O-((2-methoxy ethoxy)methyl) oxime.

Examples of suitable alkali metal hydroxides include, but are not limited to, sodium hydroxide, potassium hydroxide, and lithium hydroxide. Examples of suitable alkaline earth metal oxides include, but are not limited to, calcium oxide, magnesium oxide, barium oxide, and strontium oxide. Examples of suitable alkaline earth metal hydroxides include, but are not limited to, calcium hydroxide, magnesium hydroxide, barium hydroxide, and strontium hydroxide.

The preferred antimicrobial agent is calcium hydroxide since calcium hydroxide not only kills microorganisms but also enhances or promotes reparative bridge formation and remineralization. The reparative bridge formation dramatically increases the likelihood that a tooth that has had its pulp and/or the adjacent pink dentin exposed will survive and continue to be viable.

The antimicrobial agents, when included within the adhesive sealants of the present invention, are preferably included in a concentration of about 0.001% to about 80% by weight of the adhesive sealant composition, more preferably in a concentration of about 0.005% to about 45%, and most preferably in a concentration of about 0.01% to about 35% by weight of the adhesive sealant composition.

3. Initiators

Initiators are provided in the composition to induce polymerization of the adhesion monomer and optional dilutent monomers. The terms "initiator" and "curing agent", as used in the specification and the appended claims, include both radiant energy polymerization initiators, with or without an appropriate organic amine additive, and chemical initiators, such as a peroxide and an appropriate organic amine additive. Curing agents may be selected to be complementary to other ingredients for a selected dental procedure.

Examples of radiant energy polymerization initiators, or "photoinitiators", include, but are not limited to, camphorquinone; benzoin methyl ether; 2-hydroxy-2-methyl-1-phenyl-1-propanone; diphenyl 2, 4, 6-trimethylbenzoyl phosphine oxide; benzoin ethyl ether; benzophenone; 9, 10-anthraquinone, and mixtures or derivatives thereof.

Examples of peroxide-based chemical initiators include, but are not limited to, benzoyl peroxide, 2-butanone peroxide, lauroyl peroxide and tert-butyl peroxide.

Optional additives such as amine additives are preferred in formulating curing agents to assist the curing agents. Examples of amine additives include, but are not limited to, dimethyl amino ethyl methacrylate; tri ethyl amine; 2-dimethylamino ethanol; diethyl amino ethyl methacrylate; trihexyl amine; N,N-dimethyl-p-toluidine; N-methylethanolamine, 2,2'(p-tolyimino)diethanol, and mixtures or derivatives thereof.

The initiators or curing agents, when included within the adhesive sealants of the present invention, are included in a concentration of from about 0.05% to about 5% by weight of the adhesive sealant composition, more preferably in a concentration of about 0.1% to about 2%, and most preferably in a concentration of about 0.2% to about 1% by weight of the adhesive sealant composition. In addition to the above curing agents, other curing agents are within the contemplation of the present invention and can be found by routine experimentation by reading the disclosure and practicing the invention.

4. Fillers

Fillers can also be added, if desired, so as to function as visible light opaquers, radio-opaquers and strengtheners. Examples of suitable inorganic fillers include, but are not limited to, silicon dioxide, titanium dioxide, barium sulfate, strontium sulfate, barium chloride, strontium chloride and calcium phosphate tribasic. The fillers may be added to provide radio-opacity, minimize polymerization shrinkage and to reduce the total heat potential of polymerization.

The fillers, when included within the adhesive sealants of the present invention, are preferably included in a concentration up to about 85% by weight of the adhesive sealant composition, more preferably in a concentration of about 2% to about 70%, and most preferably in a concentration of about 5% to about 50% by weight of the adhesive sealant composition.

5. Additional Monomers

Additional monomers, also known as "diluent monomers", can also be added to adjust or impact various properties such as strength and viscosity. Examples of suitable diluent monomers include, but are not limited to, alkyl methacrylates, alkylhydroxy methacrylates and alkylamino methacrylates. Examples of suitable alkyl methacrylates include, but are not limited to, triethylene glycol dimethacrylate, polyethylene glycol dimethacrylate, and butandiol dimethacrylate. Examples of suitable alkylhydroxy methacrylates include, but are not limited to 2-hydroxyethyl methacrylate and glycerol dimethacrylate. Bis-GMA is an example of a methacrylate including both alkyl and aryl constituents. An example of a suitable alkyl amino methacrylate includes urethane dimethacrylate.

The additional or diluent monomers, if included within the adhesive sealant compositions of the present invention, are preferably included in a concentration of up to about 90% by weight of the adhesive sealant composition, more preferably in a concentration of about 5% to about 80%, and most preferably in a concentration of about 10% to about 70% by weight of the adhesive sealant composition.

C. Other Components

In addition to the hemostatic compositions that include propylhexedrine and the adhesive sealant compositions, the kits may optionally include virtually any composition used in the art of dental restorations. For example, the kits may include an antimicrobial composition separate and apart from the adhesive sealant composition which is either applied separately or which may be combined with either the hemostatic composition, the adhesive sealant composition, or both just prior to application to the exposed pulp and/or pink dentin.

The kits may also include a filling material, such as a composite restorative filler or metal amalgam, separate and apart from the adhesive sealant material, which is applied to completely fill the hole or void after sealing the pulp and/or dentin using the adhesive sealant composition disclosed herein. Preferred restorative composite filling materials are available from Ultradent Products, Inc. under the trade name PERMAFLO.

The kits may also include primers, etchants (e.g., aqueous phosphoric acid), washes and the like as needed in order to facilitate ease of use.

D. Dispensers and other Apparatus

The kits may optionally include apparatus for dispensing one or more of the compositions within the inventive kits. For example, the hemostatic composition may advantageously be applied to the pulp and/or pink dentin by means of any applicator known in the art, such as an absorbent material or a syringe. These or any other dispensers known in the art may optionally be included within the inventive kits. Once one of ordinary skill in the art appreciates the advantages provided by the inventive kits, it will become readily apparent through routine experimentation and testing how to select an appropriate dispenser for each of the compositions within the inventive kits.

In a preferred embodiment, the hemostatic composition containing propylhexedrine, e.g., propylhexedrine hydrochloride, may be applied by means of an absorbent material such as a cotton ball or pellet, which may advantageously be sized and shaped so as to be at least partially insertable within the tooth void being treated. Hence, the kits may include the aforementioned cotton ball, pellet, other absorbent material. The hemostatic composition may either be initially contained in a compartment separate from the absorbent applicator or it may be provided impregnated within the absorbent applicator. If separate, the practitioner will be able to apply an appropriate amount of the hemostatic composition to the applicator prior to application of the hemostatic composition to the pulp and/or pink dentin being treated. Of course, it is certainly within the scope of the invention to provide any other applicator, such as a syringe equipped with a needle.

The adhesive sealant composition may be provided or pre-loaded within one or more syringes. In the case where a photoinitiator is used as the sole initiator, the adhesive sealant composition may be prepackaged as a single, one-part composition for ease of use. Where it is desired to use a chemical initiator in addition to, or instead of, the photoinitiator, it will be advantageous to provide a separate storage compartment for the chemical initiator but which allows for ease of mixing of the chemical initiator and the adhesion monomer just prior to use. This may be provided, for example, by means of a double-barrelled syringe.

The kits may also include other apparatus, such as disposable tools for placing and removing the absorbent applicator for the hemostatic composition. Any tool known in the art for inserting and then removing solid objects from a void within a tooth may be included within the kits of the present invention. Examples include curved hooks or probes.

III. METHODS OF USING THE INVENTIVE KITS

The inventive kits may be utilized according to any desired method of use by the practitioner. In the case where the kit comprises a two-component kit, including a hemostatic composition and an adhesive sealant composition, the two components will advantageously be applied step-wise in succession. First, the hemostatic composition is applied to the pulp and/or dentin using any desired applicator or application means, such as an absorbent applicator or a syringe.

In a preferred embodiment, the hemostatic composition is applied to the pulp and/or dentin by means of a cotton pellet. The cotton pellet or other absorbent applicator may advantageously be applied by means of a booked or bent probe or other device capable of at least partially entering the void in the tooth being treated. The cotton pellet not only provides propylhexedrine as needed but also provides a barrier which physically maintains the blood in the vicinity of the pulp and/or dentin in order to facilitate hemostasis. It may also serve to absorb a portion of the blood or other fluid oozing from the pulp and/or pink dentin.

Upon achieving a desired level of hemostasis, the cotton pellet or other absorbent applicator is removed using any appropriate device, such as a curved hook or probe. Excess fluid is then appropriately removed such as by aspiration of the tooth and surrounding area. Prior to application of the adhesive sealant material, care should be taken to not unduly disrupt or injure the pulp and/or pink dentin so as to prevent further bleeding or oozing of fluid therefrom. In addition, care should be taken to avoid contamination of the pulp and/or pink dentin.

The adhesive sealant composition is then applied to the dentin in order to seal the dentin and, where appropriate, any exposed pulp below the dentin. Upon application of the sealant composition, it is caused to cure or polymerization using any appropriate curing means. In a preferred embodiment, the adhesive sealant composition will include a polymerization photoinitiator such that the sealant is cured or polymerized using an appropriate source of radiant energy, such as a curing lamp. If desired, multiple layers of the sealant may be applied.

In the case where an antimicrobial composition separate from the hemostatic composition and adhesive sealant composition is provided, the antimicrobial composition may be advantageously applied subsequent to hemostasis and aspiration and prior to application of the adhesive sealant material. Alternatively, it may be mixed with either or both of the hemostatic and adhesive sealant compositions.

If a restorative filling material is included separate and apart from the adhesive sealant composition, such filling material is preferably applied after appropriate application and curing of the adhesive sealant composition. In order to enhance the bond strength of the optional composite restorative filler, an acid etchant may be applied to the tooth hollow, preferably after curing and of the adhesive sealant composition.

IV. EXAMPLES OF THE PREFERRED EMBODIMENTS

Several examples of the present invention are presented as merely illustrative of some embodiments of the present invention. These examples are not to be construed as limiting the spirit and scope of the invention. When the past tense is used, the example has actually been made. When the present tense is used, the example is hypothetical in nature. Since the kits within the present invention have not actually been packaged and sold in this manner, the kits are presently hypothetical.

EXAMPLE 1

An adhesive antimicrobial sealant composition was formed having the following components, expressed in terms of weight percent:

| Component | Concentration |
| --- | --- |
| Calcium Hydroxide | 10.0% |
| Bis-Glycerol Methacrylate Phosphate | 5.0% |
| Urethane Dimethacrylate | 57.0% |
| Triethylene Glycol Dimethacrylate | 6.0% |
| Titanium Dioxide | 1.0% |
| Calcium Phosphate Tribasic | 10.0% |
| Dimethyl Amino Ethyl Methacrylate | 0.5% |
| Camphorquinone | 0.2% |
| Barium Sulfate | 10.3% |

The foregoing adhesive sealant composition was loaded into a syringe. A separate storage compartment including a hemostatic composition is associated together with the syringe containing the adhesive sealant composition to form a kit. The hemostatic composition includes 80% by weight of purified water and 20% by weight of propylhexedrine hydrochloride. The components within the kit may be used to successively provide hemostasis and then sealing of exposed pulp and/or pink dentin.

EXAMPLE 2

An adhesive antimicrobial sealant composition was formed having the following components, expressed in terms of weight percent:

| Component | Concentration |
|---|---|
| Calcium Hydroxide | 10.0% |
| Bis-Glycerol Methacrylate Phosphate | 5.0% |
| Diurethane Dimethacrylate | 59.5% |
| Triethylene Glycol Dimethacrylate | 4.0% |
| Titanium Dioxide | 1.0% |
| Calcium Phosphate Tribasic | 9.5% |
| Dimethylaminoethyl Methacrylate | 0.5% |
| Camphorquinone | 0.2% |
| Barium Sulfate | 10.3% |
| Pigments | trace |

The foregoing adhesive sealant composition was loaded into a syringe. A separate storage compartment including a hemostatic composition is associated together with the syringe containing the adhesive sealant composition to form a kit. The hemostatic composition includes 80% by weight of purified water and 20% by weight of propylhexedrine hydrochloride. The components within the kit may be used to successively provide hemostasis and then sealing of exposed pulp and/or pink dentin.

EXAMPLE 3

An adhesive antimicrobial sealant composition was formed having the following components, expressed in terms of weight percent:

| Component | Concentration |
|---|---|
| Calcium Hydroxide | 10.0% |
| Bis-Glycerol Methacrylate Phosphate | 5.0% |
| Diurethane Dimethacrylate | 58.9% |
| Triethylene Glycol Dimethacrylate | 4.0% |
| Titanium Dioxide | 1.0% |
| Calcium Phosphate Tribasic | 10.0% |
| Dimethylaminoethyl Methacrylate | 0.5% |
| Camphorquinone | 0.2% |
| Barium Sulfate | 10.3% |
| Hydroquinone | 0.1% |

The foregoing adhesive sealant composition was loaded into a syringe. A separate storage compartment including a hemostatic composition is associated together with the syringe containing the adhesive sealant composition to form a kit. The hemostatic composition includes 80% by weight of purified water and 20% by weight of propylhexedrine hydrochloride. The components within the kit may be used to successively provide hemostasis and then sealing of exposed pulp and/or pink dentin.

EXAMPLE 4

An adhesive antimicrobial dental composition is formed having the following components, expressed in terms of weight percent:

| Component | Concentration |
|---|---|
| Bis 2-Hydroxy Ethyl Methacrylate | 10.0% |
| Barium Hydroxide | 25.0% |
| Calcium Phosphate Tribasic | 5.0% |
| Benzoin Ethyl Ether | 0.4% |
| N-Methylethanol Amine | 0.5% |
| Glycerol Dimethacrylate | 59.1% |

The adhesive antimicrobial dental composition would be expected to provide a better seal than liners or pulp caps which do not include methacrylates. The composition would also be expected to seal a treated area to eliminate microorganisms in the treated area The antimicrobial agent would not be expected to be consumed during the polymerization reaction and would be expected to be capable of antimicrobial activity even after polymerization.

The foregoing adhesive sealant composition is loaded into a syringe. A separate storage compartment including a hemostatic composition is associated together with the syringe containing the adhesive sealant composition to form a kit. The hemostatic composition includes 80% by weight of purified water and 20% by weight of propylhexedrine hydrochloride. The components within the kit may be used to successively provide hemostasis and then sealing of exposed pulp and/or pink dentin.

EXAMPLE 5

An adhesive antimicrobial dental composition is formed having the following components, expressed in terms of weight percent:

| Component | Concentration |
|---|---|
| Strontium Oxide | 30.0% |
| Camphorquinone | 0.5% |
| Diethyl Amino Ethyl Methacrylate | 0.5% |
| Bis Glyceryl Methacrylate Phosphate | 69.0% |

The adhesive antimicrobial dental composition would be expected to provide a better seal than liners or pulp caps which do not include phosphate methacrylates. The composition would also be expected to seal a treated area to eliminate microorganisms in the treated area The antimicrobial agent would not be expected to be consumed during the polymerization reaction and would be expected to be capable of antimicrobial activity even after polymerization.

The foregoing adhesive sealant composition is loaded into a syringe. A separate storage compartment including a hemostatic composition is associated together with the syringe containing the adhesive sealant composition to form a kit. The hemostatic composition includes 80% by weight of purified water and 20% by weight of propylhexedrine hydrochloride. The components within the kit may be used to successively provide hemostasis and then sealing of exposed pulp and/or pink dentin.

EXAMPLE 6

An adhesive antimicrobial dental composition is formed having the following components, expressed in terms of weight percent:

| Component | Concentration |
| --- | --- |
| Cetyl Pyridinium Chloride | 4.0% |
| Strontium Chloride | 10.0% |
| 2-Hydroxy-2-Methyl-1-Phenyl-1-Propanone | 0.5% |
| Diphenyl 2,4,6-Trimethylbenzoyl Phosphine Oxide | 0.5% |
| Xanthomycin | 1.0% |
| Phosphate Ester of 4-Hydroxy Butyl Methacrylate | 29.0% |
| Butane Diol Dimethacrylate | 55.0% |

The adhesive antimicrobial dental composition would be expected to provide a better seal than liners or pulp caps which do not include phosphate methacrylates. The composition would also be expected to be stable during storage and capable of in situ polymerization upon initiation of the photoinitiator. The composition would also be expected to seal a treated area to eliminate microorganisms in the treated area. The antimicrobial agent would not be expected to be consumed during the polymerization reaction and would be expected to be capable of antimicrobial activity even after polymerization.

The foregoing adhesive sealant composition is loaded into a syringe. A separate storage compartment including a hemostatic composition is associated together with the syringe containing the adhesive sealant composition to form a kit. The hemostatic composition includes 80% by weight of purified water and 20% by weight of propylhexedrine hydrochloride. The components within the kit may be used to successively provide hemostasis and then sealing of exposed pulp and/or pink dentin.

EXAMPLE 7

An adhesive antimicrobial dental composition is formed having the following components, expressed in terms of weight percent:

| Component | Concentration |
| --- | --- |
| Penicillin N | 3.5% |
| Silicon Dioxide Fumed | 16.0% |
| Bis-Glyceryl Methacrylate Phosphate | 3.0% |
| Benzophenone | 1.0% |
| Tri Hexyl Amine | 1.5% |
| Calcium Phosphate Tribasic | 10.0% |
| Bis 2-Hydroxy Ethyl Methacrylate | 4.0% |
| Triethylene Glycol Dimethacrylate | 61.0% |

The adhesive antimicrobial dental composition would be expected to provide a better seal than liners or pulp caps which do not include phosphate methacrylates. The composition would also be expected to be stable during storage and capable of in situ polymerization upon initiation of the photoinitiator. The composition would also be expected to seal a treated area to eliminate microorganisms in the treated area. The antimicrobial agent would not be expected to be consumed during the polymerization reaction and would be expected to be capable of antimicrobial activity even after polymerization.

The foregoing adhesive sealant composition is loaded into a syringe. A separate storage compartment including a hemostatic composition is associated together with the syringe containing the adhesive sealant composition to form a kit. The hemostatic composition includes 80% by weight of purified water and 20% by weight of propylhexedrine hydrochloride. The components within the kit may be used to successively provide hemostasis and then sealing of exposed pulp and/or pink dentin.

EXAMPLE 8

An adhesive antimicrobial dental composition is formed having the following components, expressed in terms of weight percent:

| Component | Concentration |
| --- | --- |
| 4'-Sulfamoylsulfanilanilide | 1.0% |
| 1,1'-Hexamethylene Bis (5(p-Chlorophenyl) Biguanide) | 1.0% |
| Phosphate Ester of 3-Hydroxy Propyl Methacrylate | 5.0% |
| Urethane Dimethacrylate | 92.0% |
| Benzoin Ethyl Ether | 1.0% |
| 2-Dimethylaminoethanol | 1.0% |

The adhesive antimicrobial dental composition would be expected to provide a better seal than liners or pulp caps which do not include phosphate methacrylates. The composition would also be expected to be stable during storage and capable of in situ polymerization upon initiation of the photoinitiator. The composition would also be expected to seal a treated area to eliminate microorganisms in the treated area. The antimicrobial agent would not be expected to be consumed during the polymerization reaction and would be expected to be capable of antimicrobial activity even after polymerization.

The foregoing adhesive sealant composition is loaded into a syringe. A separate storage compartment including a hemostatic composition is associated together with the syringe containing the adhesive sealant composition to form a kit. The hemostatic composition includes 80% by weight of purified water and 20% by weight of propylhexedrine hydrochloride. The components within the kit may be used to successively provide hemostasis and then sealing of exposed pulp and/or pink dentin.

EXAMPLE 9

An adhesive antimicrobial dental composition is formed having the following components, expressed in terms of weight percent:

| Component | Concentration |
| --- | --- |
| Magnesium Oxide | 15.0% |
| Barium Chloride | 40.0% |
| 9,10-Anthraquinone | 0.9% |
| Triethylamine | 0.3% |
| Bis Glyceryl Methacrylate Phosphate | 43.8% |

The adhesive antimicrobial dental composition would be expected to provide a better seal than liners or pulp caps which do not include phosphate methacrylates. The composition would also be expected to be stable during storage and capable of in situ polymerization upon initiation of the photoinitiator. The composition would also be expected to seal a treated area to eliminate microorganisms in the treated area. The antimicrobial agent would not be expected to be consumed during the polymerization reaction and would be expected to be capable of antimicrobial activity even after polymerization.

The foregoing adhesive sealant composition is loaded into a syringe. A separate storage compartment including a hemostatic composition is associated together with the syringe containing the adhesive sealant composition to form a kit. The hemostatic composition includes 80% by weight of purified water and 20% by weight of propylbexedrine hydrochloride. The components within the kit may be used to successively provide hemostasis and then sealing of exposed pulp and/or pink dentin.

EXAMPLE 10

To any of the foregoing kits is added a cotton swab or pellet or other absorbent applicator, which may be used to facilitate the application of the hemostatic composition to the exposed pulp and/or pink dentin of the tooth being treated.

EXAMPLE 11

To any of the foregoing kits is added a syringe applicator, which may be used to facilitate the application of the hemostatic composition to the exposed pulp and/or pink dentin of the tooth being treated.

EXAMPLE 12

To any of the foregoing kits is added a restorative composite dental composition appropriate for filling cavities.

EXAMPLE 13

To any of the kits made according to Example 12 is added an acid etchant, such as an aqueous solution of phosphoric acid (30% by weight), to facilitate bonding of the restorative composite dental composition to dentin.

V. SUMMARY

Based on the foregoing, the present invention provides compositions, methods, and kits that enable more reliable sealing and adhesion to the dentinal tissue so as to provide a a reliable barrier to the ingress of bacterial into the pulp and/or pink dentin and thereby prevent infection of the tooth.

More specifically, the invention provides compositions, methods, and kits which can arrest the bleeding of the pulp and/or pink dentin subsequent to exposure of the pulp and/or pink dentin and preparatory to the application of an adhesive sealant or filling material to the dentin.

The invention further provides compositions, methods, and kits which include a hemostatic agent that is capable of arresting the bleeding of exposed pulp and/or pink dentin which does not result in the death of the pulp.

The invention yet provides compositions, methods, and kits which include an adhesive liner, capping, and/or filling material capable of forming a strong and reliable seal against the dentin in order to form a reliable barrier against ingress of microorganisms in the pulp and/or pink dentin.

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A kit for providing hemostasis and sealing of exposed pulp or dentin comprising:

a hemostatic composition including propylhexedrine; and an adhesive sealant composition including at least one polymerizable material capable of adhering to dentin.

2. A kit for providing hemostasis and sealing of exposed pulp or dentin as defined in claim 1, further including an applicator for applying the hemostatic composition to at least one of the exposed pulp or dentin.

3. A kit for providing hemostasis and sealing of exposed pulp or dentin as defined in claim 2, wherein the applicator for applying the hemostatic composition comprises a cotton pellet sized so as to at least partially fit within a hollow in a tooth.

4. A kit for providing hemostasis and sealing of exposed pulp or dentin as defined in claim 2, wherein the applicator for applying the hemostatic composition comprises a syringe.

5. A kit for providing hemostasis and sealing of exposed pulp or dentin as defined in claim 2, wherein the applicator for applying the adhesive sealant composition comprises a syringe.

6. A kit for providing hemostasis and sealing of exposed pulp or dentin as defined in claim 1, further including an applicator for applying the adhesive sealant composition to at least one of the exposed pulp or dentin.

7. A kit for providing hemostasis and sealing of exposed pulp or dentin as defined in claim 1, wherein the propylhexedrine is in the form of a salt.

8. A kit for providing hemostasis and sealing of exposed pulp or dentin as defined in claim 7, wherein the propylhexedrine is propylhexedrine hydrochloride.

9. A kit for providing hemostasis and sealing of exposed pulp or dentin as defined in claim 8, wherein the hemostatic composition comprises an aqueous solution of propylhexedrine hydrochloride.

10. A kit for providing hemostasis and sealing of exposed pulp or dentin as defined in claim 8, wherein the hemostatic composition comprises an aqueous solution which includes propylhexedrine hydrochloride in a range from about 10% to about 99% by weight of the aqueous solution.

11. A kit for providing hemostasis and sealing of exposed pulp or dentin as defined in claim 8, wherein the hemostatic composition comprises an aqueous solution which includes propylhexedrine hydrochloride in a range from about 50% to about 95% by weight of the aqueous solution.

12. A kit for providing hemostasis and sealing of exposed pulp or dentin as defined in claim 8, wherein the hemostatic composition comprises an aqueous solution which includes propylhexedrine hydrochloride in a range from about 70% to about 90% by weight of the aqueous solution.

13. A kit for providing hemostasis and sealing of exposed pulp or dentin as defined in claim 12, wherein the alkyl methacrylate is selected from the group consisting of bis 2-hydroxy ethyl methacrylate phosphate, phosphate ester of p-hydroxyphenyl methacrylamide, phosphate ester of 3-hydroxy propyl methacrylate, phosphate ester of 4-hydroxy butyl methacrylate, bis-glycerol methacrylate phosphate, and mixtures of the foregoing.

14. A kit for providing hemostasis and sealing of exposed pulp or dentin as defined in claim 13, wherein the polymerization photoinitiator is at least one of camphorquinone, benzoin methyl ether, 2-hydroxy-2-methyl-1-phenyl-1-propanone, diphenyl-2,4,6-trimethylbenzoyl phosphine oxide, benzoin ethyl ether, benzophenone, or 9,10-anthraquinone.

15. A kit for providing hemostasis and sealing of exposed pulp or dentin as defined in claim 12, wherein the adhesive sealant composition further comprises at least one polymerization photoinitiator which initiates polymerization of the alkyl methacrylate upon irradiating the adhesive sealant composition with radiant energy.

16. A kit for providing hemostasis and sealing of exposed pulp or dentin as defined in claim 12, wherein the adhesive sealant composition further comprises up to 90% by weight of at least one additional monomer, which is at least one of an alkyl methacrylate, an alkyl hydroxy methacrylate, an alkyl amino methacrylate, or Bis-GMA.

17. A kit for providing hemostasis and sealing of exposed pulp or dentin as defined in claim 12, wherein the adhesive sealant composition further comprises up to 85% by weight of a filler, which is at least one of silicon dioxide, titanium dioxide, barium sulfate, strontium sulfate, barium chloride, strontium chloride, or calcium phosphate tribasic.

18. A kit for providing hemostasis and sealing of exposed pulp or dentin as defined in claim 17, wherein the antimicrobial agent includes at least one of calcium hydroxide or calcium oxide.

19. A kit for providing hemostasis and sealing of exposed pulp or dentin as defined in claim 12, wherein the adhesive sealant composition further comprises at least one antimicrobial agent selected from the group consisting of alkali metal hydroxides, alkaline earth metal oxides, alkaline earth metal hydroxides, organohalogens, antibiotics, and mixtures of the foregoing.

20. A kit for providing hemostasis and sealing of exposed pulp or dentin as defined in claim 1, wherein the adhesive sealant composition comprises at least one alkyl methacrylate including at least one oxyphosphorus group having a formula selected from the group consisting of

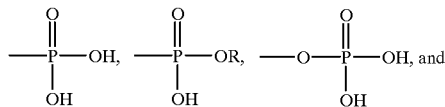

-continued

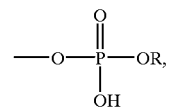

wherein R is at least one or alkyl or aryl.

21. A method for providing hemostasis and sealing of exposed pulp and dentin comprising:

contacting at least one of exposed tooth pulp or dentin with a hemostatic composition which includes a hemostatic effective amount of propylhexedrine; and applying an adhesive sealant composition to at least a portion of the exposed dentin so as to seal at least one of the exposed pulp or dentin, the adhesive sealant composition including at least one polymerizable material capable of adhering to dentin.

22. A method for providing hemostasis of exposed pulp or dentin as defined in claim 21, wherein the hemostatic composition is applied to at least one of the exposed pulp or dentin by means of a cotton pellet applicator.

23. A method for providing hemostasis of exposed pulp or dentin as defined in claim 21, further including the step of removing the hemostatic composition and other fluid from the exposed pulp or dentin by means of aspiration.

24. A method for providing hemostasis and sealing of exposed pulp or dentin as defined in claim 21, further including the step of removing the hemostatic composition and other fluid from the exposed pulp or dentin by means of aspiration prior to applying the adhesive sealant.

* * * * *

UNITED STATES PATENT AND TRADEMARK OFFICE
CERTIFICATE OF CORRECTION

PATENT NO. : 6,309,221 B1
DATED : October 30, 2001
INVENTOR(S) : Steven D. Jensen Page 1 of 1

It is certified that error appears in the above-identified patent and that said Letters Patent is hereby corrected as shown below:

Column 4,
Line 7, after "advantageously" insert -- be --
Line 46, change "prevent" to -- present --

Column 5,
Line 2, change "bacterial" to -- bacteria --

Column 7,
Line 36, change "provide" to -- provided --

Column 11,
Line 45, change "booked" to -- hooked --

Column 14,
Line 13, insert -- . -- after " area"
Line 48, insert -- . -- after " area"

Column 17,
Line 38, delete "a" after "provide"
Line 38, change "bacterial" to -- bacteria --

Signed and Sealed this

Ninth Day of April, 2002

*Attest:*

JAMES E. ROGAN
*Attesting Officer*    *Director of the United States Patent and Trademark Office*